United States Patent
Thomas et al.

(10) Patent No.: US 10,194,657 B2
(45) Date of Patent: Feb. 5, 2019

(54) ANTIMICROBIAL COMPOSITIONS

(71) Applicants: Joseph Paul Thomas, Edgewood, KY (US); Zsolt Istvan Hertelendy, Mason, OH (US); Michael Lisle Howell, Mason, OH (US)

(72) Inventors: Joseph Paul Thomas, Edgewood, KY (US); Zsolt Istvan Hertelendy, Mason, OH (US); Michael Lisle Howell, Mason, OH (US)

( * ) Notice: Subject to any disclaimer, the term of this patent is extended or adjusted under 35 U.S.C. 154(b) by 0 days.

(21) Appl. No.: 14/491,358

(22) Filed: Sep. 19, 2014

(65) Prior Publication Data

US 2015/0079203 A1   Mar. 19, 2015

Related U.S. Application Data

(60) Provisional application No. 61/879,688, filed on Sep. 19, 2013, provisional application No. 61/903,645, filed on Nov. 13, 2013.

(51) Int. Cl.
| | | |
|---|---|---|
| *A61K 36/00* | (2006.01) | |
| *A61K 36/752* | (2006.01) | |
| *A61K 36/53* | (2006.01) | |
| *A01N 37/44* | (2006.01) | |
| *A01N 31/02* | (2006.01) | |
| *A01N 41/02* | (2006.01) | |
| *A01N 25/30* | (2006.01) | |

(52) U.S. Cl.
CPC .............. *A01N 37/44* (2013.01); *A01N 25/30* (2013.01); *A01N 31/02* (2013.01); *A01N 41/02* (2013.01)

(58) Field of Classification Search
None
See application file for complete search history.

(56) References Cited

U.S. PATENT DOCUMENTS

| | | | |
|---|---|---|---|
| 4,511,488 A | 4/1985 | Matta | |
| 5,942,480 A * | 8/1999 | Prevost | A61L 2/18 510/161 |
| 6,177,070 B1 | 1/2001 | Lynch | |
| 6,585,961 B1 * | 7/2003 | Stockel | A61K 8/0291 424/49 |
| 7,314,857 B2 * | 1/2008 | Madhyastha | A01N 43/16 435/252.1 |
| 7,582,681 B2 * | 9/2009 | Schmaus | A01N 31/02 424/44 |
| 2003/0125224 A1 | 7/2003 | Seitz, Jr. et al. | |
| 2004/0091558 A1 * | 5/2004 | Lutz | A01N 35/02 424/745 |
| 2004/0208842 A1 * | 10/2004 | Ritchie | A61K 8/41 424/70.21 |
| 2005/0106191 A1 | 5/2005 | Kobayashi et al. | |
| 2007/0265352 A1 | 11/2007 | Roeding et al. | |
| 2009/0175806 A1 * | 7/2009 | Modak | A61K 8/0208 424/58 |
| 2010/0260865 A1 | 10/2010 | Kritzler | |
| 2011/0054026 A1 * | 3/2011 | Doyle | A01N 31/16 514/558 |
| 2012/0328548 A1 | 12/2012 | Touitou | |
| 2013/0230609 A1 | 9/2013 | Modak et al. | |
| 2015/0079203 A1 | 3/2015 | Thomas et al. | |

FOREIGN PATENT DOCUMENTS

| | | | | |
|---|---|---|---|---|
| CN | 102876479 A | 1/2013 | | |
| EP | 2356982 A2 * | 8/2011 | ........... | A61K 9/0014 |
| EP | 2356982 A3 | 4/2012 | | |
| JP | H02-48523 A | 2/1990 | | |
| JP | H10-130203 A | 5/1998 | | |
| JP | H10-511999 A | 11/1998 | | |
| JP | 2004-307484 A | 11/2004 | | |
| JP | 2006-526664 A | 11/2006 | | |
| JP | 2008-105990 A | 5/2008 | | |
| JP | 2008-195688 A | 8/2008 | | |
| JP | 2012-177901 A | 9/2012 | | |
| JP | 2013-170160 A | 9/2013 | | |
| WO | 2009/124392 A1 | 10/2009 | | |

OTHER PUBLICATIONS

Website document entitled "Carvacrol" (available at https://wikipedia.en/wiki/Carvacrol). Downloaded Apr. 16, 2016.*
Ben Arfa et al. (2006) Lett. Appl. Microbiol. 43: 149-154.*
Tallarida (2001) J. Pharma. Exper. Therapeutics 298: 865-872.*
International Search Report; PCT/US14/56575; Dated Dec. 12, 2014; 3 pages.
Written Opinion of the International Searching Authority; PCT/US14/56575; Dated Dec. 12, 2014; 10 pages.
Feng Zhou et al., "Synergistic Effect of Thymol and Carvacrol Combined with Chelators and Organic Acids against *Salmonella typhimurium*", Journal of Food Protection, vol. 70, No. 7, Jul. 1, 2007, pp. 1704-1709.
Supplementary European Search Report of the European Patent Office, Issued in European Application No. 14845813.6-1454 / 3046540; dated Jan. 4, 2017; 8 pages.
International Search Report and Written Opinion of the International Searching Authority for International Patent App. No. PCT/US2017/052914 dated Dec. 8, 2017; 7 pages.

* cited by examiner

*Primary Examiner* — Christopher R Tate
*Assistant Examiner* — Russell G Fiebig
(74) *Attorney, Agent, or Firm* — Ulmer and Berne, LLP

(57) ABSTRACT

Antimicrobial compositions providing synergistic antimicrobial effects against a variety of bacterial, viral and fungal organisms are described. Methods for using the antimicrobial compositions and products containing the antimicrobial compositions are also described herein.

11 Claims, No Drawings

ANTIMICROBIAL COMPOSITIONS

CROSS-REFERENCE TO RELATED APPLICATIONS

This application claims the priority benefit of U.S. Provisional Patent Application Ser. No. 61/879,688, "Antimicrobial Compositions," filed Sep. 19, 2013, and U.S. Provisional Patent Application Ser. No. 61/903,645, "Antimicrobial Compositions," filed Nov. 13, 2013, both of which are hereby expressly incorporated by reference in their entirety.

TECHNICAL FIELD

The present disclosure generally relates to antimicrobial compositions.

BACKGROUND

Pathogenic microorganisms, including, for example, bacteria, viruses, and fungi, are responsible for a host of human diseases, ranging from more minor ailments, such as upper and lower respiratory tract infections, to potentially fatal infections. Major progress has been made in combating diseases caused by pathogenic microorganisms with the development of copious pharmaceutical and non-pharmaceutical agents to be used in treatments. For example, chemical-based agents may be used for external treatment (e.g., on a hard surface) to prevent contamination and transmission to humans. While agents have been developed that are generally effective against various pathogens, there is increasing evidence that the use of such agents has certain limitations that warrant concern. Specifically, certain strains of pathogenic microorganisms have become increasingly resistant to one or more antimicrobials, thereby rendering the standard courses of treatment ineffective. Accordingly, higher doses of antimicrobial treatments may be required to achieve efficacy, which can result in undesirable side effects and toxicity to both humans and the environment. Also, many disinfectants do not persist in antimicrobial activity once applied on surfaces.

Accordingly, it would be desirable to achieve antimicrobial compositions that can effectively treat bacteria, viral or fungal contamination or prevent such contamination on various surfaces while remaining safe for human contact and the environment, and that retains antimicrobial activity for several days after application.

SUMMARY

In one embodiment, an antimicrobial composition comprising a synergistic antimicrobial effective amount of a chelating agent and one or more surfactants.

In another embodiment, an antimicrobial composition includes a synergistic antimicrobial effective amount of one of 1,2-hexanediol or 1,2-pentanediol and one or more surfactants.

In yet another embodiment, an antimicrobial composition includes 5% by volume/volume or more of 1,2-hexanediol. The antimicrobial composition is active against at least one of *E. coli, S. aureus, P. aeruginosa, S. enterica, B. pertussis* and *Saccharomyces cerevisiae*.

In still another embodiment, an antimicrobial composition includes a synergistic antimicrobial effective amount of sodium dodecyl sulfate (SDS) and an oil component. The oil component includes one or more of tea tree oil, oregano oil, lemon grass oil, lavender oil, citronella oil, *eucalyptus* oil, clove oil, cinnamon oil, and peppermint oil.

In yet still another embodiment, an antimicrobial composition includes a synergistic antimicrobial effective amount of a mixture of 1,2-pentanediol and 1,2-hexanediol.

In yet still another embodiment, an antimicrobial composition includes a synergistic antimicrobial effective amount of a mixture of 1,2-hexanediol and a bleaching agent.

In still yet another embodiment, an antimicrobial composition includes a synergistic antimicrobial effective amount of: a chelating agent; a straight chain 1,2-alkanediol; one or more surfactants and a biocidal terpenoid. The chelating agent includes an ethylenediamine tetraacetic acid or salts thereof (EDTA). The antimicrobial composition is active against one or more of *Escherichia coli* (*E. coli*), *Staphylococcus aureus* (*S. aureus*), *Pseudomonas aeruginosa* (*P. aeruginosa*), *Salmonella enterica* (*S. enterica*), *Bordetella pertussis* (*B. pertussis*) and *Saccharomyces cerevisiae*

DETAILED DESCRIPTION

In the following detailed description, reference is made to specific embodiments in which the invention may be practiced. These embodiments are described in sufficient detail to enable those skilled in the art to practice the invention. Other embodiments may be utilized and structural, logical, and chemical changes may be made without departing from the scope of the present invention. The following detailed description is, therefore, not to be taken in a limiting sense, and the scope of the present invention is defined only by the appended claims and equivalents thereof.

Effective treatment for bacterial, viral and fungal infections is necessary, particularly in settings like hospitals, clinics, medical research centers, nursing homes, schools and athletic facilities such as gymnasiums, health clubs, and spas. Hospitals, schools, athletic facilities and similar institutions are always looking for effective solutions to reduce or prevent the spread of ancillary infections such as *Staphylococcus aureus* (*S. aureus*). One such example is commonly known as methicillin-resistant *Staphylococcus aureus*, or MRSA. Outbreaks of MRSA or other bacterial infections are major concerns for medical facilities, schools, nursing homes, etc. To curb the likelihood of such unforeseen outbreaks, hospitals, schools and other institutions have implemented the use of disinfectants and training protocols to reduce such risks. However, such disinfectants do not necessarily offer the antimicrobial benefits or lasting effectiveness desired by these institutions. The present disclosure describes antimicrobial compositions and methods of using such antimicrobial compositions that provide such desired advantages and benefits.

Certain antimicrobial compositions described herein provide synergistic advantages over traditional compositions. For example in one embodiment, an antimicrobial composition can have a synergistic antimicrobial effective amount of a chelating agent, such as ethylenediamine tetraacetic acid or salts thereof (EDTA), and one or more surfactants. In certain embodiments, the antimicrobial composition can have from about 0.1% to about 3% (wt./vol.) of EDTA; in certain embodiments from about 0.2% to about 2.5% (wt./vol.) of EDTA; in certain embodiments from about 0.5% to about 1.5% (wt./vol.) of EDTA; and in certain embodiments from about 0.7% to about 1.0% (wt./vol.) of EDTA. In certain embodiments, the antimicrobial composition can have from about 0.01% to about 2% (wt./vol.) of the one or more surfactants; in certain embodiments from about 0.05% to about 1.5% (wt./vol.) of the one or more surfactants; in certain embodiments from about 0.1% to about 1% (wt./vol.) of the one or more surfactants; and in certain embodiments from about 0.2% to about 0.8% (wt./vol.) of the one or more surfactants. In certain embodiments, the antimicrobial composition can have from about 0.01% to about 2% (vol./vol.) of the one or more surfactants; in certain embodiments from about 0.05% to about 1.5% (vol./vol.) of the one or more surfactants; in certain embodiments from about 0.1% to about 1% (vol./vol.) of the one or more surfactants; and in certain embodiments from about 0.2% to about 0.8% (vol./vol.) of the one or more surfactants. It will be appreciated that when an antimicrobial composition is added to a product (such as a disinfectant product) that the overall concentration levels of a surfactant (e.g., SDS), or other constituents described herein, in those products may be higher than the concentration of levels described herein with respect to the antimicrobial composition.

The one or more surfactants can be selected from anionic, cationic, nonionic, or zwitterionic surfactants. Suitable surfactants can include sodium dodecyl sulfate (SDS), a Triton® surfactant (e.g., Triton® X-100), tetradecyldimethyl (3-sulfopropyl)-ammonium hydroxide inner salt, or combinations thereof. Other suitable surfactants may also be contemplated.

In certain embodiments, an antimicrobial composition does not include a peroxide (e.g., hydrogen peroxide).

In certain embodiments, the antimicrobial compositions can have a synergistic antimicrobial effective amount of an oil component. Suitable examples of oil components can include tea tree oil, oregano oil, lemon grass oil, lavender oil, citronella oil, *eucalyptus* oil, clove oil, cinnamon oil, peppermint oil, and any combination thereof. In certain embodiments, an antimicrobial composition can include up to about 5% (vol./vol.) of an oil component. In certain embodiments, an antimicrobial composition can include about 0.5% (vol./vol.) or less of an oil component; in certain embodiments, an antimicrobial composition can include about 0.3% (vol./vol.) or less of an oil component; in certain embodiments, an antimicrobial composition can include from about 0.05% to about 0.25% (vol./vol.) of an oil component; and in certain embodiments, an antimicrobial composition can include from about 0.07% to about 0.1% (vol./vol.) of an oil component. Other suitable oil components may be contemplated, including oils that contain a biocidal terpenoid.

In certain embodiments, an antimicrobial composition can have a synergistic antimicrobial effective amount of a straight chain 1,2-alkanediol having a chain length in the range of 5 to 10 carbon atoms. Such 1,2-alkanediols include, 1,2-pentanediol, 1,2-hexanediol, 1,2-heptanediol, 1,2-octanediol, 1,2-nonanediol, and 1,2-decanediol. In certain embodiments, the antimicrobial composition can include a mixture of straight chain 1,2-alkanediols, for example, 1,2-pentanediol and 1,2-hexanediol.

In certain embodiments, an antimicrobial composition can have a synergistic antimicrobial effective amount of a biocidal terpenoid. Suitable examples of such biocidal terpenoids can include thymol, carvacrol, eugenol, limonene, and any combination thereof. In certain embodiments, an antimicrobial composition can include up to about 5% (wt./vol.) of a biocidal terpenoid. In certain embodiments, an antimicrobial composition can include about 0.5% (wt./vol.) or less of a biocidal terpenoid; in certain embodiments, an antimicrobial composition can include about 0.3% (wt./vol.) or less of a biocidal terpenoid; and in certain embodiments, an antimicrobial composition can include from about 0.05% to about 0.1% (wt./vol.) of a biocidal terpenoid.

In certain embodiments, an antimicrobial composition can include a synergistic antimicrobial effective amount of one of 1,2-pentanediol or 1,2-hexanediol and one or more surfactants. Such an antimicrobial composition can achieve the designed benefits and advantages as described herein. In one such embodiment, the antimicrobial composition can have from about 1.0% to about 10% (vol./vol.) of either the 1,2-hexanediol or 1,2-pentanediol and from about 0.01% to about 2.0% (wt./vol.) of the one or more surfactants. In another such embodiment, the antimicrobial composition can have from about 1.5% to about 8% (vol./vol.) of either the 1,2-hexanediol or 1,2-pentanediol and from about 0.05% to about 1.5% (wt./vol.) of the one or more surfactants. In another embodiment, the antimicrobial composition can have from about 2% to about 5% (vol./vol.) of either the 1,2-hexanediol or 1,2-pentanediol and from about 0.1% to about 1.0% (wt./vol.) of the one or more surfactants. In another embodiment, the antimicrobial composition can have about 3% (vol./vol.) of either the 1,2-hexanediol or 1,2-pentanediol.

In certain embodiments, an antimicrobial composition can include 5% by (vol./vol.) or more of 1,2-hexanediol, such that the composition is effective against a bacteria strain of at least one of *Escherichia coli* (*E. coli*), *Staphylococcus aureus* (*S. aureus*), *Pseudomonas aeruginosa* (*P. aeruginosa*), *Bordetella pertussis* (*B. pertussis*) and *Salmonella enterica* (*S. enterica*). The *S. enterica* can be *Salmonella enterica* subsp. *enterica* (ex Kauffmann and Edwards) Le Minor and Popoff serovar *Choleraesuis* (ATCC® 10708™). Such antimicrobial compositions can also be effective against fungal organisms (e.g., yeast strains), such as *Saccharomyces cerevisiae*. Further, such antimicrobial compositions can also be effective against *Aspergillus*. The effectiveness of such antimicrobial compositions described herein is further detailed below. In certain embodiments, the antimicrobial composition can have about 10% (vol./vol.) of the 1,2-hexanediol. Such an antimicrobial composition can further include a synergistic antimicrobial effective amount of a chelating agent, such as EDTA. Such antimicrobial compositions can have from about 0.1% to about 3% (wt./vol.) of EDTA; in certain embodiments from about 0.2% to about 2.5% (wt./vol.) of EDTA; in certain embodiments from about 0.5% to about 1.5% (wt./vol.) of EDTA; and in certain embodiments from about 0.7% to about 1.0% (wt./vol.) of EDTA.

In certain embodiments, an antimicrobial composition can include a synergistic antimicrobial effective amount of SDS and an oil component. Suitable examples of oil components can include tea tree oil, oregano oil, lemon grass oil, lavender oil, citronella oil, *eucalyptus* oil, clove oil, cinnamon oil, peppermint oil, and any combination thereof. In certain embodiments, an antimicrobial composition can include about 0.5% (vol./vol.) or less of an oil component; in certain embodiments, an antimicrobial composition can include about 0.3% (vol./vol.) or less of an oil component; in certain embodiments, an antimicrobial composition can include from about 0.05% to about 0.25% (vol./vol.) of an oil component; and in certain embodiments, an antimicrobial composition can include from about 0.07% to about 0.1% (vol./vol.) of an oil component. Other suitable oil components may be contemplated, including oils that contain a biocidal terpenoid.

In certain embodiments, an antimicrobial composition can include a synergistic antimicrobial effective amount of a mixture of 1,2-pentanediol and 1,2-hexanediol. Such antimicrobial compositions can further include a synergistic effective amount of one or more surfactants. The one or more surfactants can include SDS and/or a Triton® surfactant. Such antimicrobial composition can further include a synergistic antimicrobial effective amount of an oil component. Suitable examples of oil components can include tea tree oil, oregano oil, lemon grass oil, lavender oil, citronella oil, *eucalyptus* oil, clove oil, cinnamon oil, peppermint oil, and any combination thereof. In certain embodiments, an antimicrobial composition can include about 0.5% (vol./vol.) or less of an oil component; in certain embodiments, an antimicrobial composition can include about 0.3% (vol./vol.) or less of an oil component; in certain embodiments, an antimicrobial composition can include from about 0.05% to about 0.25% (vol./vol.) of an oil component; and in certain embodiments, an antimicrobial composition can include from about 0.07% to about 0.1% (vol./vol.) of an oil component. Other suitable oil components may be contemplated, including oils that contain a biocidal terpenoid.

In certain embodiments, an antimicrobial composition can include 1,2-hexanediol and a bleaching agent (e.g., Clorox®). Such an antimicrobial composition can be effective against a bacteria strain of at least one of *Escherichia coli* (*E. coli*), *Staphylococcus aureus* (*S. aureus*), *Pseudomonas aeruginosa* (*P. aeruginosa*), *Bordetella pertussis* (*B. pertussis*) and *Salmonella enterica* (*S. enterica*). Such antimicrobial compositions can also be effective against fungal organisms (e.g., yeast strains), such as *Saccharomyces cerevisiae*. Further, such antimicrobial compositions can also be effective against *Aspergillus*. In certain embodiments, the antimicrobial composition can have about 5% (vol./vol.) of the 1,2-hexanediol. In certain embodiments, the antimicrobial composition can have from about 1% (wt./vol.) to about 10% (wt./vol.) of the bleaching agent. In certain embodiments, the antimicrobial composition can have from about 1% (wt./vol.) to about 5% (wt./vol.) of the bleaching agent. In certain embodiments, the bleaching agent can be chlorine-based. In certain embodiments, the bleaching agent can be peroxide-based. In certain embodiments, the bleaching agent can include sodium hypochlorite, calcium hypochlorite, chlorine dioxide, hydrogen peroxide, sodium percarbonate, sodium perborate, sodium dithionite, sodium borohydride, or combinations thereof. Other suitable bleaching agents are also contemplated.

In certain embodiments, an antimicrobial composition can have a pH from about 7 to about 9; and in certain embodiments can have a pH of about 8. The pH of an antimicrobial composition can be modified or maintained through inclusion of a buffering agent. Suitable buffering agents can include tris-hydrochloride, tris citrate, and combinations thereof. Other suitable buffering agents may be contemplated. In certain embodiments, an antimicrobial composition can have about 10 mM to about 100 mM of a buffering agent. In certain embodiments, an antimicrobial composition can from about 25 mM to about 50 mM of a buffering agent.

Application of Antimicrobial Compositions

The antimicrobial compositions described herein can be employed in a variety of applications, including as disinfectants, cell lysing agents, prophylaxis against contamination, etc. Such compositions are effective in decontaminating and protecting against contamination of surfaces that are susceptible to contamination by microorganisms or formation of biofilm coatings thereon. While the antimicrobial compositions described herein may be highly effective against viral and fungal infections, such compositions are also effective against bacterial components, such as *E. coli*, *S. aureus*, *P. aeruginosa*, and *S. enterica*. Such antimicrobial compositions are also effective against fungal organisms (e.g., yeast strains), such as *Saccharomyces cerevisiae*. Further, such antimicrobial compositions can also be effective against *Aspergillus*.

Effectiveness of the antimicrobial compositions can be defined as a percentage of bacterial cells destroyed or killed when subjected to the composition. For example, the antimicrobial compositions can be at least 99.99% effective against certain bacterial strains such as *S. aureus*. This means that for every 1 million *S. aureus* cells subjected to the antimicrobial composition all but about 100 *S. aureus* cells remain. In certain embodiments, the antimicrobial compositions can be at least 99.999% effective against *S. aureus*. In certain embodiments, the antimicrobial compositions can be at least 99.9999% effective against *S. aureus*. In certain embodiments, the antimicrobial compositions can be at least 99.99999% effective against *S. aureus*. In certain embodiments, the antimicrobial compositions can be at least 99.999999% effective against *S. aureus*. For purposes of this disclosure "subjected to" can mean treating a surface having been exposed to a bacterial strain and/or pretreating a surface with the antimicrobial composition that may eventually come into contact with a bacterial strain. A surface can include a variety of objects including tables, beds, countertops, clothing, human skin, medical or exercise equipment and other surfaces that can potentially become contaminated.

In addition to the general effectiveness of the antimicrobial compositions described herein with respect to bacterial strains, such compositions remain effective after certain periods of duration. For example, such antimicrobial compositions may be at least 99.99% effective against *S. aureus* in at most about 1 minute after being subjected to the composition. Such antimicrobial compositions may be at least 99.99% effective against *S. aureus* in at most about 10 minutes after being subjected to the composition. In certain embodiments, the antimicrobial composition may be at least 99.99% effective against *S. aureus* about 24 hours after being subjected to the composition; in certain embodiments, the antimicrobial composition may be at least 99.99% effective against *S. aureus* about 48 hours after being subjected to the composition; in certain embodiments, the antimicrobial composition may be at least 99.99% effective against *S. aureus* about 72 hours (3 days) after being subjected to the composition; in certain embodiments, the antimicrobial composition may be at least 99.99% effective against *S. aureus* about 120 hours (5 days) after being subjected to the composition; in certain embodiments, the antimicrobial composition may be at least 99.99% effective against *S. aureus* about 7 days after being subjected to the composition; and in certain embodiments, the antimicrobial composition may be at least 99.99% effective against *S. aureus* about 12 days after being subjected to the composition. The lasting or persistent effectiveness of the antimicrobial compositions described herein provides substantial benefits to medical institutions in the battle of reducing or eliminating the spread of such bacterial strains such as MRSA.

EXAMPLES

Antimicrobial composition examples were prepared using the methodology described below and the effectiveness of certain antimicrobial compositions was measured with respect to exposure to *S. aureus*.

*S. aureus* strains were obtained having various designations. MRSA strains that were tested have a designation of ATCC® 43300. Other MRSA strains were also tested having a designation of ATCC® 6538 and NRS385 (also designated as USA300-0114). Finally, other non-MRSA examples were also tested and have a designation of ATCC® BA-977.

Nutrient broth and agar plates were prepared to test the effectiveness of the comparative examples against the designated *S. aureus* stains. A liter of nutrient broth was prepared using 5 gm of peptone (Difco Laboratories lot #7169), 3 gms of beef extract (Difco Laboratories lot #136314 XB), and 5 gms sodium chloride (NaCl) (Fisher Scientific lot #116736).

*S. aureus* strains were grown overnight at 37° C. to a density corresponding to 0.8 $OD_{600}$. Then, 100 uL of the bacterial suspensions (approximately $10^7$ cells) were placed in 1.5 ml Eppendorf tubes and gently mixed. A respective antimicrobial composition was added to the cell suspensions at a volume of 100 uL followed by mixing on a rocker for 10 minutes. Each comparative antimicrobial composition outlined in Tables 1 and 2 below includes components prepared at the concentrations specified from pure solutions. Control tubes containing 100 uL of nutrient broth were also tested in lieu of the comparative antimicrobial compositions. From these suspensions, serial dilutions were also performed to allow for cell enumeration. A control consisting of 10% sodium hypochlorite (Clorox®) was prepared in sterile water.

Following 10 minutes of incubation (while being gently rocked), 10 uL of bacterial suspensions containing comparative antimicrobial compositions were pipetted onto nutrient broth agar plates (each plate having 100 mm surface area) containing 100 uL of nutrient broth on the agar surface. Cells were spread across the plate surface using a conventional sterilized glass spreader. Cell colony counts were enumerated. Plates containing serially diluted controls were enumerated, and the number of colony forming units present prior to adding comparative antimicrobial compositions was then calculated.

Enumeration was performed and quantified as no effect (no to little difference relative to control), mild effect (noticeable 1000-fold reduction in estimated colonies), good effect (log reduction of 4 to 5, corresponding to cell counts of 100 to 10 colonies, or a maximum log reduction of 6 to 7 evidenced by no growth evident to 10 or fewer, or no colonies, respectively. The log reductions were converted into effectiveness percentages as shown in Tables 1 and 2.

Certain tubes containing bacteria with certain comparative examples were kept, re-plated and enumerated in the same manner 5 days to determine if greater or lesser efficacy occurred over time, if a log reduction of at least 6 was not noted with the initial tests.

The results of the initial testing and enumeration are set forth below in Table 1. The antimicrobial compositions enumerated for 5 days are presented in Table 2. Each of the Antimicrobial Composition Examples in Tables 1 and 2 was tested against MRSA strains having a designation of ATCC® 43300 and the effectiveness percentages reflect the effectiveness of those examples against ATCC® 43300. Some of the Antimicrobial Composition Examples in Tables 1 and 2 were also tested against MRSA strains having a designation of ATCC® 6538, NRS385 (also designated as USA300-0114) and non-MRSA strains having a designation of ATCC® BA-977, and the resulting effectiveness percentages were the same or higher than those reported below with respect to MRSA strains designated ATCC® 43300.

TABLE 1

| Antimicrobial Composition Examples | Formulations | Effectiveness (after 10 minutes of exposure) |
|---|---|---|
| Control 1 (Comparative) | 10% Clorox ® bleach[1]<br>Remainder: deionized water | 99.9999% |
| A | 10% (vol./vol.) 1,2-hexanediol<br>Remainder: deionized water | 99.9999% |
| B | 5% (vol./vol.) 1,2-hexanediol<br>Remainder: deionized water | 99.999% |
| C | 5% (vol./vol.) 1,2-hexanediol<br>0.1% (wt./vol.) SDS[2]<br>0.1% (vol./vol.) TTO[3]<br>Remainder: deionized water | 99.9999% |
| D | 5% (vol./vol.) 1,2-hexanediol<br>0.1% (wt./vol.) SDS<br>0.25% (vol./vol.) TTO<br>Remainder: deionized water | 99.9999% |
| E | 5% (vol./vol.) 1,2-hexanediol<br>1.46% (wt./vol.) EDTA[4]<br>Remainder: deionized water | 99.9999% |
| F | 5% (vol./vol.) 1,2-hexanediol<br>1.46% (wt./vol.) EDTA<br>1% (wt./vol.) SDS<br>Remainder: deionized water | 99.9999% |
| G | 2% (vol./vol.) 1,2-hexanediol<br>1.46% (wt./vol.) EDTA<br>0.1% (wt./vol.) SDS<br>Remainder: deionized water | 99.999%-99.9999% |
| H | 2% (vol./vol.) 1,2-hexanediol<br>0.1% (wt./vol.) SDS<br>0.1% (wt./vol.) Thymol<br>Remainder: deionized water | 99.999% |
| I | 3% (vol./vol.) 1,2-hexanediol<br>1.46% (wt./vol.) EDTA<br>0.1% (wt./vol.) SDS<br>0.1% (vol./vol.) TTO<br>Remainder: deionized water | 99.9999% |
| J | 2% (vol./vol.) 1,2-hexanediol<br>1.46% (wt./vol.) EDTA<br>0.1% (wt./vol.) SDS<br>0.1% (vol./vol.) TTO<br>Remainder: deionized water | 99.999% |
| K | 1% (vol./vol.) 1,2-hexanediol<br>1.46% (wt./vol.) EDTA<br>0.1% (wt./vol.) SDS<br>0.1% (vol./vol.) TTO<br>Remainder: deionized water | 99.99% |
| L | 2% (vol./vol.) 1,2-hexanediol<br>1.46% (wt./vol.) EDTA<br>0.1% (wt./vol.) SDS<br>0.1% (vol./vol.) Oregano Oil<br>Remainder: deionized water | 99.9999% |
| M | 5% (vol./vol.) 1,2-hexanediol<br>0.1% (vol./vol.) TTO<br>Remainder: deionized water | 99.9999% |
| N | 5% (vol./vol.) 1,2-hexanediol<br>1.46% (wt./vol.) EDTA<br>1% (wt./vol.) SDS<br>Remainder: deionized water | 99.999% |
| O | 0.5% (vol./vol.) 1,2-hexanediol<br>1.46% (wt./vol.) EDTA<br>1% (wt./vol.) SDS<br>Remainder: deionized water | 99.99% |
| P | 3% (vol./vol.) 1,2-pentanediol<br>2% (vol./vol.) 1,2-hexanediol<br>0.1% (vol./vol.) Triton ®[5]<br>0.1% (vol./vol.) TTO<br>Remainder: deionized water | 99.999%-99.9999% |
| Q | 3% (vol./vol.) 1,2-pentanediol<br>2% (vol./vol.) 1,2-hexanediol<br>Remainder: deionized water | 99.99% |
| R | 3% (vol./vol.) 1,2-pentanediol<br>2% (vol./vol.) 1,2-hexanediol<br>0.1% (vol./vol.) TTO<br>0.1% (wt./vol.) SDS<br>Remainder: deionized water | 99.9999% |
| S | 3% (vol./vol.) 1,2-pentanediol<br>2% (vol./vol.) 1,2-hexanediol<br>0.1% (wt./vol.) SDS | 99.9999% |

TABLE 1-continued

| Antimicrobial Composition Examples | Formulations | Effectiveness (after 10 minutes of exposure) |
|---|---|---|
| T | 0.1% (wt./vol.) SDS<br>1.46% (wt./vol.) EDTA<br>Remainder: deionized water | 99.99% |
| U | 0.1% (wt./vol.) SDS<br>2.92% (wt./vol.) EDTA<br>Remainder: deionized water | 99.999% |
| V | 0.1% (wt./vol.) SDS<br>0.73% (wt./vol.) EDTA<br>0.1% (vol./vol.) Oregano Oil<br>Remainder: deionized water | 99.9999% |
| W | 0.1% (wt./vol.) SDS<br>1.46% (wt./vol.) EDTA<br>0.1% (vol./vol.) Oregano Oil<br>Remainder: deionized water | 99.9999% |
| X | 0.1% (wt./vol.) SDS<br>0.73% (wt./vol.) EDTA<br>0.1% (vol./vol.) Carvacrol<br>Remainder: deionized water | 99.9999% |
| Y | 0.1% (wt./vol.) SDS<br>0.1% (vol./vol.) Oregano Oil<br>Remainder: deionized water | 99.999% |
| Z | 1% (wt./vol.) Zwitterionic surfactant[6]<br>1.46% (wt./vol.) EDTA<br>Remainder: deionized water | 99.9999% |
| AA | 5% (vol./vol.) 1,2-hexanediol<br>1.46% (wt./vol.) EDTA<br>0.1% (wt./vol.) SDS<br>0.1% (vol./vol.) Carvacrol<br>Remainder: deionized water | 99.9999%-99.99999% |
| BB | 3% (vol./vol.) 1,2-hexanediol<br>1.46% (wt./vol.) EDTA<br>0.1% (wt./vol.) SDS<br>0.1% (vol./vol.) Carvacrol<br>Remainder: deionized water | 99.9999%-99.99999% |

[1]Clorox ® bleach is sodium hypochlorite
[2]SDS—Sodium dodecyl sulfate (Gibco lot # BKH2O8)
[3]TTO—Tea tree oil
[4]EDTA—ethylenediamine tetraacetic acid or salts thereof
[5]Triton ® X-100 (Acros Organis lot # A0302505)
[6]Tetradecyldimethyl(3-sulfopropyl)-ammonium hydroxide inner salt (TCI lot # DLBRG-OK)

As noted above in Table 1, the effectiveness of each of the given antimicrobial composition examples was measured after 10 minutes of having the bacteria stain subject to the respective compositions. Conventional antimicrobial compositions do not demonstrate effectiveness after such a short duration and typically can take several hours, if not days, to achieve the level of effectiveness displayed by Antimicrobial Composition Examples A-BB. In fact, Antimicrobial Composition Examples A, C, D, E, F, I, L, M, R, S, V, W, X, AA, and BB achieved equivalent or better results than the Control 1 example (Clorox® bleach, 10%) a known antimicrobial agent which has harsher and more toxic properties than these respective antimicrobial compositions examples.

When Antimicrobial Composition Examples AA and BB were subjected to S. aureus strains in equal parts per volume with the respective compositions (e.g., 100 uL sample containing S. aureus strain and 100 uL of the respective comparative example) the effectiveness of each of Antimicrobial Composition Example AA and BB was 99.99999% within 10 minutes of treatment. It was also discovered that Antimicrobial Composition Examples AA and BB were at least 99.99999% effective within 1 minute of treatment.

It is also noted that for each of Antimicrobial Composition Examples A-BB, plates were also prepared with the respective antimicrobial compositions and then subjected to the bacteria strains. The compositions and bacteria strains were prepared in the same manner as described above and the enumeration was calculated using the same method as described above. The effectiveness of each of the Antimicrobial Composition Examples A-BB after 10 minutes was the same as above noted in Table 1, where the plates were contaminated with the bacteria strain and then treated with the antimicrobial compositions.

TABLE 2

| Antimicrobial Composition Examples | Formulations | Effectiveness (after 5 days of exposure) |
|---|---|---|
| Control 1 | 10% Clorox ® bleach<br>Remainder: deionized water | None |
| Control 2 | 70% Ethanol | None |
| Control 3 | Deionized water | None |
| Control 4 | 3% (wt./vol.) hydrogen peroxide<br>Remainder: deionized water | None |
| AA | 5% (vol./vol.) 1,2-hexanediol<br>1.46% (wt./vol.) EDTA<br>0.1% (wt./vol.) SDS<br>0.1% (vol./vol.) Carvacrol<br>Remainder: deionized water | 99.99999% |
| BB | 3% (vol./vol.) 1,2-hexanediol<br>1.46% (wt./vol.) EDTA<br>0.1% (wt./vol.) SDS<br>0.1% (vol./vol.) Carvacrol<br>Remainder: deionized water | 99.9999% |
| CC | 1.46% (wt./vol.) EDTA<br>0.1% (wt./vol.) SDS<br>0.1% (vol./vol.) Carvacrol<br>Remainder: deionized water | 99.99% |
| DD | 2.92% (wt./vol.) EDTA<br>0.1% (wt./vol.) SDS<br>0.1% (vol./vol.) Carvacrol<br>Remainder: deionized water | 99.99% |
| B | 5% (vol./vol.) 1,2-hexanediol<br>Remainder: deionized water | 99.99%-99.999% |
| EE | 5% (vol./vol.) 1,2-hexanediol<br>1% (wt./vol.) Clorox ® bleach | 99.999999% |
| FF | 5% (vol./vol.) 1,2-hexanediol<br>5% (wt./vol.) Clorox ® bleach | 99.999999% |
| GG | 5% (vol./vol.) 1,2-hexanediol<br>10% (wt./vol.) Clorox ® bleach | 99.999999% |
| HH | 5% (vol./vol.) 1,2-hexanediol<br>5% (wt./vol.) hydrogen peroxide | 99.999999% |

For each of Antimicrobial Composition Examples B and AA-HH 100 uL of each antimicrobial composition was pipetted into individual wells of sterile 12-well plates and rotated to allow coating of each bottom. Control wells contained 100 uL of sterile water. The lids were removed and each antimicrobial composition was allowed to evaporate from 24 hours to as many as 12 days.

Cell suspensions of overnight bacterial cultures were prepared as noted above. Approximately $10^7$ cells/100 uL were added to each well. Cell suspensions were also serially diluted suspensions were placed into control wells to allow for enumeration. Once cells were added, the plates were shaken on a rotary shaker for 10 minutes. From each well, 10 uL of suspension was plated onto nutrient broth agar plates containing 100 uL of nutrient broth, spread, incubated and enumerated as above.

Antimicrobial Composition Examples B and AA-HH illustrate the lasting and persistent effectiveness of certain antimicrobial compositions with respect to S. aureus strains. The benefit of such lasting effectiveness reduces the number of times that surfaces need to be treated prior to such surfaces being contacted by additional patients or medical personal. In fact, Antimicrobial Composition Examples B and AA-HH achieved long lasting effectiveness (maintained effectiveness against S. aureus strains after 5 days), which was not the case for the Control 1 example (Clorox® bleach, 10%), Control 2 example (70% ethanol), and Control 4 example (3% hydrogen peroxide), known antimicrobial agents. Controls 1 and 2 did not provide any more effectiveness after 5 days as Control 1 (deionized water). It is believed that with respect to Antimicrobial Composition Examples EE-HH that the hexanediol component may preserve biocidal activity of the bleaching agent through possible stabilization of the active ingredients.

Also, with respect to Antimicrobial Composition Examples B and EE-HH, it was discovered that these respective compositions have an effectiveness equivalent to or the same as those reported in Table 2 when subject to at least 12 days of exposure. As such, these respective compositions had not only a high effectiveness, but unexpected persistence much greater than other known antimicrobial compositions.

In addition to serving as disinfectants the antimicrobial compositions can also serve as lysing agents. Bacterial strains were prepared as above from overnight cultures. The cells were placed in Eppendorf tubes in 1.0 ml volumes and centrifuged at 12,000 rpm for 1 minute. The supernatant was removed and the cell pellet was reconstituted with 100 uL of test substances followed by 10 minutes of incubation at room temperature on a rotating platform.

The cell suspension was re-centrifuged at 12,000×g for 5 minutes to separate the soluble and insoluble protein fractions. The supernatant was transferred to a new 1.5 ml tube, being careful not to remove insoluble debris. The soluble and insoluble fractions were analyzed by SDS-PAGE for protein content using a representative acrylamide gel. As a marker for cellular lytic activity, a Western blot was performed on each cell fraction to determine reactivity of a soluble intracellular protein. For those comparative examples shown in Table 3 below, specific proteins presented indicated that cell lysis had occurred. The specific Antimicrobial Composition Examples tested showing such cell lysis are shown below in Table 3.

TABLE 3

| Antimicrobial Composition Examples | Formulations | Cell Lysis Occurs? |
| --- | --- | --- |
| AA | 5% (vol./vol.) 1,2-hexanediol<br>1.46% (wt./vol.) EDTA<br>0.1% (wt./vol.) SDS<br>0.1% (vol./vol.) Carvacrol<br>Remainder: deionized water | Yes |
| BB | 3% (vol./vol.) 1,2-hexanediol<br>1.46% (wt./vol.) EDTA<br>0.1% (wt./vol.) SDS<br>0.1% (vol./vol.) Carvacrol<br>Remainder: deionized water | Yes |
| CC | 1.46% (wt./vol.) EDTA<br>0.1% (wt./vol.) SDS<br>0.1% (vol./vol.) Carvacrol<br>Remainder: deionized water | Yes |
| DD | 2.92% (wt./vol.) EDTA<br>0.1% (wt./vol.) SDS<br>0.1% (vol./vol.) Carvacrol<br>Remainder: deionized water | Yes |
| II | 20% (vol./vol.) 1,2-hexanediol<br>Remainder: deionized water | Yes |

As illustrated in Table 3 above, Comparative Antimicrobial Composition Examples AA-DD and HH provided cell lysing when introduced to bacterial cells. Each of the Comparative Antimicrobial Composition Examples in Table 3 was tested against MRSA strains having a designation of ATCC® 43300. Some of the Comparative Antimicrobial Composition Examples in Table 3 were also tested against MRSA strains having a designation of ATTC® 6538 and NRS385 (also designated as USA300-0114) and non-MRSA strains having a designation of ATCC® BA-977, and the lysing results were the same for those reported above with respect to MRSA strains designed ATCC® 43300.

The dimensions and values disclosed herein are not to be understood as being strictly limited to the exact numerical values recited. Instead, unless otherwise specified, each such dimension is intended to mean both the recited value and a functionally equivalent range surrounding that value.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in the document shall govern.

The foregoing description of embodiments and examples has been presented for purposes of description. It is not intended to be exhaustive or limiting to the forms described. Numerous modifications are possible in light of the above teachings. Some of those modifications have been discussed and others will be understood by those skilled in the art. The embodiments were chosen and described for illustration of various embodiments. The scope is, of course, not limited to the examples or embodiments set forth herein, but can be employed in any number of applications and equivalent articles by those of ordinary skill in the art. Rather it is hereby intended the scope be defined by the claims appended hereto.

What is claimed is:

1. An antimicrobial composition comprising:
    a) from about 0.2% to about 3%, by weight per volume, of ethylenediamine tetraacetic acid (EDTA) or salts thereof;
    b) from about 1% to about 5% by volume per volume of 1,2-hexanediol;
    c) from about 0.01% to about 2.0%, by weight per volume, of sodium dodecyl sulfate (SDS);
    d) from about 0.05% to about 0.5%, by weight per volume of a biocidal terpenoid selected from the group consisting of thymol, carvacrol, eugenol, and limonene; and
    e) the balance being water; and
       wherein the antimicrobial composition exhibits antimicrobial and bactericidal efficacy against one or more of *Escherichia coli* (*E. coli*), *Staphylococcus aureus* (*S. aureus*), *Pseudomonas aeruginosa* (*P. aerugi-* nosa), *Salmonella enterica* (*S. enterica*), *Bordetella pertussis* (*B. pertussis*) and *Saccharomyces cerevisiae*.

2. The antimicrobial composition of claim 1 being at least 99.99% effective against *S. aureus* after 10 minutes of being applied to a surface.

3. The antimicrobial composition of claim 1 being at least 99.99% effective against *S. aureus* after 24 hours of being applied to a surface.

4. The antimicrobial composition of claim 1 being at least 99.99% effective against *S. aureus* up to 5 days after being applied to a surface.

5. The antimicrobial composition of claim 1 being at least 99.99% effective against *S. aureus* up to 12 days after being applied to a surface.

6. The antimicrobial composition of claim 1 comprising:
   a) about 1.5%, by weight per volume, of ethylenediamine tetraacetic acid (EDTA) or salts thereof;
   b) about 3% by volume per volume of 1,2-hexanediol;
   c) about 0.1%, by weight per volume, of sodium dodecyl sulfate (SDS);
   d) about 0.1%, by weight per volume of a biocidal terpenoid selected from the group consisting of thymol, carvacrol, eugenol, and limonene; and
   e) the balance being water.

7. The antimicrobial composition of claim 1 does not include a peroxide.

8. The antimicrobial composition of claim 1 capable of decontaminating surfaces susceptible to contamination by microorganisms.

9. The antimicrobial composition of claim 1 capable of decontaminating surfaces susceptible to the formation of a biofilm coating thereon.

10. A disinfectant product comprising the antimicrobial composition of claim 1.

11. A method for disinfecting a surface comprising applying an effective amount of the antimicrobial composition of claim 1 to a surface in need thereof.

* * * * *